US008278352B2

(12) United States Patent
Ren et al.

(10) Patent No.: US 8,278,352 B2
(45) Date of Patent: Oct. 2, 2012

(54) PESTICIDE COMPOSITIONS AND METHODS

(75) Inventors: YongLin Ren, Nicholls (AU); Colin Waterford, Macgregor (AU); ByungHo Lee, Deajeon (KR)

(73) Assignee: Commonwealth Scientific & Industrial Research Organisation, Campbell (AU)

( * ) Notice: Subject to any disclaimer, the term of this patent is extended or adjusted under 35 U.S.C. 154(b) by 959 days.

(21) Appl. No.: 11/722,657

(22) PCT Filed: May 25, 2005

(86) PCT No.: PCT/AU2005/000741
§ 371 (c)(1),
(2), (4) Date: May 6, 2008

(87) PCT Pub. No.: WO2006/066308
PCT Pub. Date: Jun. 29, 2006

(65) Prior Publication Data
US 2009/0012158 A1    Jan. 8, 2009

(30) Foreign Application Priority Data
Dec. 24, 2004 (AU) ............................. 2004907399

(51) Int. Cl.
*A01N 59/24* (2006.01)
(52) U.S. Cl. .................. 514/515; 514/519; 424/607
(58) Field of Classification Search ................. None
See application file for complete search history.

(56) References Cited

U.S. PATENT DOCUMENTS

| 3,279,985 A * | 10/1966 | Katsaros et al. ............. 514/515 |
| 4,743,620 A * | 5/1988 | Hodgin ........................ 514/515 |
| 6,720,352 B1 * | 4/2004 | Rodriguez-Kabana ....... 514/451 |
| 6,913,805 B2 * | 7/2005 | Harlowe et al. ............. 428/35.7 |
| 2004/0029961 A1 * | 2/2004 | Von Krosigk et al. ........ 514/494 |
| 2004/0047914 A1 | 3/2004 | Baeumert et al. |
| 2006/0086284 A1 * | 4/2006 | Zhang et al. ............... 106/15.05 |

FOREIGN PATENT DOCUMENTS

| DE | 197 47 640 A1 | 5/1999 |
| EP | 1 093 721 A1 | 10/2000 |
| JP | 58-035101 | 3/1983 |
| JP | 03-153607 | 7/1991 |
| JP | 6-039811 | 2/1994 |
| JP | 9-157116 | 6/1997 |
| WO | WO 93/13659 | 7/1993 |
| WO | WO 96/01051 | 1/1996 |
| WO | WO 02/074089 A1 | 9/2002 |
| WO | WO 03/061384 A1 | 7/2003 |
| WO | WO 2006061842 A2 * | 6/2006 |

OTHER PUBLICATIONS

Haritos, V.S. & Dojchinov, G,. "Cytochrome c oxidase inhibition in the rice weevil *Sitophilus oryzae* (L.) by formate, the toxic metabolite of volatile alkyl formates," Comparative Biochemistry and Physiology Part C 136: 135-143 (2003), p. 142.*
Messenger, B. & Braun, A., "Alternatives to Methyl Bromide for the Control of Soil-Born Diseases and Pests in California," Pest Management Analysis and Planning Program, 55 pp. (Sep. 2000), pp. 16-17.*
Soderstrom et al. "Fumigants as Treatment for Harvested Citrus Fruits Infested with *Asynonchus godmani* (Coleoptera: Curculionidae)." J. Econ. Entomol. 1992, vol. 84(3):939-941.
Vincent, et al. "Hydrogen Phosphide and Ethyl Formate: Fumigation of Insects Infesting Dates and Other Dried Fruits." J. Econ. Entomol., 1972 vol. 65(6):1667-1669.
Weller, et al. "Cut flower disinfestation: Assessment of replacement fumigants for methyl bromide." Postharvest biology and technology, 1998, vol. 14:325-333.
Sanon, et al. "Analysis of the insecticidal activity of methylisothiocyanate on *Callosobruchus maculates* (F.)(Coleoptera: Bruhidae) and its parasitoid *Dinarmus basalis* (Rodani)(Hymenoptera: Pteromalidae)" J. Stored Porducts Research 2002, vol. 38:129-138.
May 9, 2012 European Examination Report in corresponding EP Appln. No. 05 741 918.6.
Hassall, Kenneth A., The Biochemistry and Uses of Pesticides, 2nd Edition, 1990, Chapter 11 Non-systemic organic fungicides, pp. 286-298, 312-314.
Cremlyn, R.J., Agrochemicals Preparation and Mode of Action, John Wiley & Sons, 1991, pp. 140-143, 149-150, 155-156, 283-286, 299-307.
Material Safety Data Sheet (MSDS), Bronson and Jacobs, Mar. 30, 2010, Ethyl Formate, 8 pages.
Drobnica, L. et al., Chapter 22, The chemistry of the NCS group, from The chemistry of cyanates and their thio derivatives Part 2, John Wiley & Sons, 1977, pp. 1003-1006, 1008-1012, 1014-1016, 1018-1029.

* cited by examiner

*Primary Examiner* — David J Blanchard
*Assistant Examiner* — Daniel F Coughlin
(74) *Attorney, Agent, or Firm* — Merchant & Gould P.C.

(57) ABSTRACT

New pesticide compositions comprising an alkyl formate and an isothiocyanic ester are described, as are methods of delivering fumigants and methods of pest control using a combination of fumigants.

9 Claims, 9 Drawing Sheets

|   | Insect cages |
|---|---|
| ● | Thermal sensor |
| O | Gas sampling ports |

PESTICIDE COMPOSITIONS AND METHODS

The present invention relates to new pesticide compositions comprising an alkyl formate and isothiocyanic ester, methods of delivering fumigants and methods of pest control using a combination of fumigants.

BACKGROUND OF THE INVENTION

Fumigants are widely used for the disinfestation, and protection against infestation, that is usually required to protect particulate commodities (such as grain) and other stored products (including durable and perishable foodstuffs or cut flower), porous bulk materials (for example, soil or timber) and spaces (either empty buildings or building containing commodities). An ideal fumigant should be toxic to insects, psocids, mites, nematodes, bacteria, fungi and their spores, viruses and moulds and other pest biota. It should be effective in low concentrations. It should ideally have a low absorption by materials in the fumigated region. It should have a low phytotoxicity to commodities. It should have a low mammalian chronic toxicity and leave either no residue or an inert residue. In addition, the ideal fumigant should present no difficulties as far as safe handling is concerned, and it should not adversely affect the commodity or space that is being fumigated.

No fumigant meets all of these "ideal" criteria. The two fumigants most commonly used in the fumigation of grain, other particulate materials, fruit and timer are phosphine and methyl bromide. However use of methyl bromide is due to be phased out in Australia and other developed countries after 2005. Carbon disulphide was recently proposed as an alternative to these fumigants (WO 93/13659) but is no longer registered for use as a fumigant in New South Wales, Australia. As a result, phosphine is expected to become the only registered fumigant available for farm use in Australia.

Phosphine is the preferred fumigant for grain stored and the like because it is effective against grain pest and leaves little residue (which is essentially a harmless phosphate). However, phosphine is spontaneously combustible when its concentration exceeds a relatively low value, and is unable to kill all stages of insects in a short period when used at acceptable concentrations.

Fumigation with phosphine requires a long (>5 days) exposure in sealed bins at temperatures above 15° C. The many existing farm bins are unsealed, and are therefore unsuitable for effective fumigation, as concentrations cannot be maintained for the time required for total insect control. The overreliance on phosphine and unsealed bins in Australia has resulted in (1) a higher frequency of resistance, (2) dangerous practices, and (3) grain delivered to grain depots containing live insects and un-reacted aluminium phosphide residues.

Alkyl formates such as ethyl formate and methyl formate have a long history of use as fumigants for stored products. Ethyl formate is currently registered as a fumigant for dried fruit in Australia and is now being investigated as an alternative fumigant for grain stored in unsealed farm bins in Australia. Care must be taken when working with alkyl formatea to keep concentrations in the structure to below the flammable level. This is done by controlling the rate of vaporisation to maintain an effective concentration of the alkyl formate for a sufficient time in the structures by avoiding accumulation of liquid alkyl formate at the bottom of the stored grain structure.

Cyanogenic compounds such as hydrogen cyanide and cyanogen chloride, chlorine and arsenical gases have all been used separately with more or less success as fumigating agents, germicides, disinfectants and for the extermination of insects and animals over time.

Cyanogen gas ($C_2N_2$) has been known as a deadly poison and was recently discovered to be suitable for use as a fumigant (WO 96/01051).

Dichlorvos is a kind of organophosphorus and organochlorine pesticide. Dichlorvos has poor penetration in grains and leaves long-term residues. There are also problems with insects becoming resistant to dichlorvos.

Isothiocyanate esters are generally presented as their crystalline solids. Typically delivery of the isothiocyanate ester fumigants is by sublimation of the solid crystals following from their high vapour pressures. Isothiocyanic esters dissolved in sulphuryl fluoride are also able to be transported. Following evaporation of the sulphuryl fluoride, crystals of the isothiocyanate ester form on the surfaces of structures or commodities. The isothiocyanate ester crystals can then act as a fumigant by sublimation in the usual way.

Other fumigants that have been used against grain pests include acrylonitrile, carbon disulphide, carbon tetrachloride, chloropicrin, ethylene dibromide, ethylene dichloride, ethylene oxide and sulphuryl fluoride.

It will be noted that none of the "conventional" fumigants have ideal fumigant properties and it is phosphine which is set to become the only registered fumigant available for farm use in Australia.

For many years there has been a constant search for new fumigants and there is no doubt that the quest for improved fumigants will continue. There is a particularly urgent requirement for the development of multi-functional grain treatments for on-farm use which should ideally be inexpensive and easy to handle and administer, particularly in unsealed storage containers such as farm bins.

SUMMARY OF THE INVENTION

The present invention seeks to provide new fumigant compositions and methods by means of which reliable control of insects, psocids, mites, nematodes, fungi and their spores, bacteria, viruses, moulds and other pest biota is possible as viable alternatives to the conventional fumigants. The present invention further seeks to provide new fumigant compositions comprising a synergistically acting combination of liquids or gases which are stable when applied together and may be stored for lengths of time.

In one broad form, the present invention provides a fumigant composition comprising an alkyl formate and an isothiocyanic ester. That is, the present inventors have surprisingly discovered that alkyl formates and isothiocyanic esters act synergistically.

In another broad form, the present invention provides a method of enhancing the efficacy of isothiocyanic esters comprising the step of combining the isothiocyanic ester with an effective amount of an alkyl formate.

In yet another broad form, the present invention provides a method of enhancing the efficacy of ethyl formate comprising the step of combining the ethyl formate with an effective amount of an isothiocyanic ester.

In another broad form, the present invention provides a method for improving the delivery of isothiocyanic esters comprising dissolving the isothiocyanic ester in an alkyl formate to form a fumigant composition and vapourising or otherwise propelling the composition.

In a further broad form, the present invention provides a method of fumigation, comprising the step of applying an alkyl formate and an isothiocyanic ester in gaseous form or in solution to a commodity and/or structure and/or space.

In a preferred embodiment, the fumigant composition further comprises a diluent, excipient or carrier. The fumigant may be provided in solution or in association with a carrier gas. Preferably the carrier gas is an inert gas and also preferably the carrier gas has a low oxygen concentration. In a preferred embodiment of the invention the carrier gas includes or is applied in an environment containing carbon dioxide.

In a preferred form, the commodity includes grain, seed, meat, fruit, dried fruit, vegetables, timber, plants, cut flowers and soil.

Preferably, the commodity includes a silo or like structure containing bulk grain (such as wheat) or the like, for quarantine disinfestations of imported produce and horticulture, and a room, premises, appliance or the like for dental, medical and/or veterinary application.

The fumigant composition is particularly suitable for use in open farm bins and silos, although it is found to be efficacious in a structure, vessel or container of any shape.

In a preferred embodiment, the fumigant is able to control one or more of a range of biota, including viruses, insects, spiders, mites, nematodes, bacteria, moulds, fungi and their spores.

In an embodiment of the invention the humidity and/or pressure within an environment within which said fumigant composition is applied is adjusted to control the characteristics (such as increased toxicity and/or synergistic effects) of said fumigant compositions.

The alkyl formates for use in the compositions and methods of the invention are preferably ethyl formate and methyl formate. In a more preferred embodiment the alkyl formate is ethyl formate, particularly when food stuffs are required to be fumigated. In the main, reference is made to ethyl formate as the preferred alkyl formate throughout the description which follows. However, it will be understood that methyl formate can be used as well in many of the compositions and methods of the invention.

The isothiocyanic esters for use in the compositions and methods of the invention are preferably lower alkyl, lower alkenyl, phenyl or benzyl isothiocyanate esters which may be optionally substituted. More preferably the isothiocyanic esters are methyl, ethyl, propyl, isopropyl, butyl, secbutyl, isobutyl or t-butyl, allyl, methylallyl, benzyl or phenyl. Optional substituents to the alkyl, benzyl or phenyl groups may include halogens including chloro, fluoro, bromo or iodo, methyl or ethyl, methoxy or ethoxy, cyano or nitro. Most preferably the isothiocyanic esters are methyl isothiocyanate and allyl isothiocyanate. In the main, reference is made to methyl isothiocyanate as the preferred isothiocyanate ester throughout the description which follows. However, it will be understood that allyl isothiocyanate and other related isothiocyanates can be used as well in the compositions and methods of the invention. For example, allyl isothiocyanate has better food tolerance and its use is less likely to be an issue in certain applications to foodstuffs.

Throughout this specification and the claims which follow, unless the context requires otherwise, the word "comprise", and variations such as "comprises" or "comprising", will be understood to imply the inclusion of a stated integer or step or group of integers or steps but not the exclusion of any other integer or step or group of integers or steps.

BRIEF DESCRIPTION OF THE DRAWINGS

The present invention will become more fully understood from the following detailed description of preferred but non-limiting embodiments thereof described hereinafter in connection with various examples outlining experimental procedures by the inventors, in connection with the accompanying drawings wherein.

DETAILED DESCRIPTION OF PREFERRED EMBODIMENTS

Figure 1:
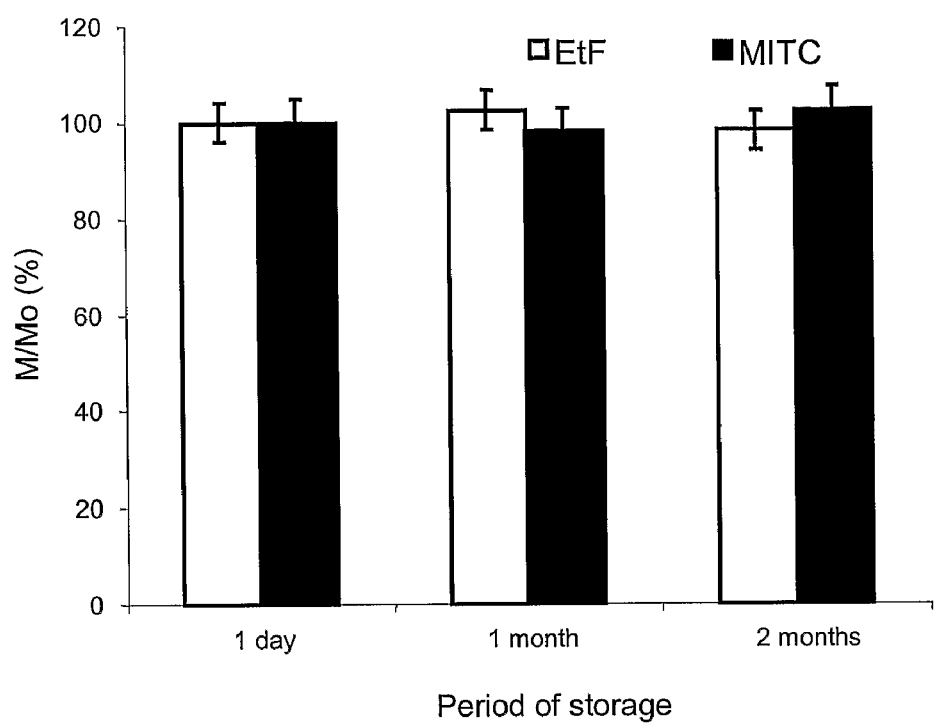
FIG. 1 graphically represents the stability of a formulation of ethyl formate and methyl isothiocyanate stored at 25° C. for 2 months at intervals of 1 day, 1 month and 2 months. M/Mo is the percentage of the original fumigant present after different periods of storage.

Ethyl formate is a naturally occurring substance commonly found in soil, the ocean and vegetation. It is found in a whole variety of plant and animal products, such as fruits and vegetables, beer, wine and spirits, tuna, meat, muscles, cheese and breads. Some grains and cereals such as barley have measurable amounts of ethyl formate present in concentrations of up to 1 mg/kg.

Ethyl formate is a odourless liquid (bp 54° C.) and has a pleasant, aromatic odour. It can be made by reacting ethanol with formic acid, themselves naturally occurring chemicals. On use as a fumigant, ethyl formate is hydrolysed or metabolised back to these naturally occurring chemicals. Formic acid and ethanol can be present in considerable levels in cereal grains in amounts of up to 300 mg/kg or higher.

Humans are constantly exposed to naturally occurring ethyl formate in a wide range of foods and therefore it is not surprising that ethyl formate is considered to have low toxicity to mammals when exposed chronically through the diet. Added to this is the common metabolic pathway in the breakdown of ethyl formate by hydrolysis to formic acid and ethanol which allows for higher occupational exposure limits for ethyl formate as alternatives to phosphine or methyl bromide.

Ethyl formate has been shown to have very rapid action against stored grain insects making it useful for rapid disinfestation of stored products including grain and fruit and vegetable treatment.

Methyl formate may also be used in the compositions and methods of the invention. It is slightly more efficacious as a fumigant than ethyl formate, however use of methyl formate for food and food products is not desirable due to the toxicity of methanol, one of its decomposition products.

Surprisingly, the present inventors have found that compositions of alkyl formate with isothiocyanic esters show markedly improved rates of disinfestation of grain in quicker times and lower concentrations when compared to the toxicity of alkyl formate alone, isothiocyanic esters alone or what might be expected with simple additive mixtures of an alkyl formate and an isothiocyanic ester.

The amount of isothiocyanic ester required to impart an improved effect on the alkyl formate fumigant formulations is relatively small. In a preferred embodiment the ratio of alkyl formate to isothiocyanic ester is up to 40% w/w isothiocyanic ester, more preferably up to 20% w/w, still more preferably up to 10% w/w and most preferably about 5% w/w isothiocyanic ester. Lower concentrations of isothiocyanic ester are preferred to minimise problems associated with isothiocyanic ester toxicity to mammals and residues thereof. Any smaller amounts of isothiocyanic esters can be used provided that it provides a synergistic effect, generally observed to begin at about 0.5% w/w isothiocyanic ester.

The fumigant compositions of the invention are prepared by dissolving the isothiocyanic ester in the alkyl formate. Ethyl formate and methyl isothiocyanate were found to be stable when formulated and stored at 25° C. for over two months. Similar results are found for combinations of ethyl and methyl formates with the various isothiocyanic esters. This allows for the fumigant compositions to be formulated in bulk and made available for transportation to the site of application. It will also be understood that the individual components can be intimately mixed on site prior to fumigation or applied simultaneously or sequentially to the commodity or structure.

The insect species studied were laboratory strains of the rice weevil *Sitophilus oryzae* present as the egg, larvae, pupae or adult and mixed aged cultures thereof in bulk stores of wheat. At concentrations of 5.9 mg/L, ethyl formate alone was found to be inactive on the adults of *Sitophilus oryzae* at 25° C. and 24 hours fumigation. In comparison, addition of 5% methyl isothiocyanate resulted in 99% mortality of the adults under the same conditions. Against other concentrations of ethyl formate, the 5% methyl isothiocyanate enriched compositions also showed strong synergistic effects across the spectrum of mixed aged cultures of *Sitophilus oryzae*.

Residue studies of fumigated wheat over 7 days were found to have negligible quantities of methyl isothiocyanate and ethyl formate residues, the fumigants declining to background levels without aeration.

Fumigation rates and plumule lengths were determined on representative samples taken before and after fumigation. It was found that the ethyl formate/methyl isothiocyanate formulations do not effect either germination (7-day count) or plumule length of barley, wheat and sorghum. Nor did the formulations of the invention effect germination of oats, maize, canola and peas.

The improved effect of alkyl formates and isothiocyanic esters was also evident in formulations mixed with a carrier gas. The carrier gas may be an inert gas and conveniently may have a low oxygen concentration. Carbon dioxide is the preferred carrier gas and it is thought that the carbon dioxide increases the respiration rate of insects and other biota and thus would increase the rate at which the ethyl formate and methyl isothiocyanate enters the pest respiratory system. The carrier gas has the added advantage of lowering the flash point of the ethyl formate vapour, and is generally found to be non-flammable when the ethyl formate is present in concentrations of up to about 16-19%.

The ethyl formate+isothiocyanic ester formulations of the invention may be presented in liquid carbon dioxide or as a liquid to gaseous carbon dioxide or other such carrier gas as would be known to those skilled in the art. For example, 16.7% by weight of a 95:5 mixture of ethyl formate+methyl isothiocyanate in 83.3% by weight of carbon dioxide contained in a pressure cylinder can be applied as a gas to the commodity or structure being fumigated (see, for example, the methods in WO03/061384). The carbon dioxide has the added advantage of acting as a solvent/propellant to disperse the chemicals as aerosol particles. Flow through techniques may further assist in the fumigation methods involving carrier gases. Allyl isothiocyanate, methyl isothiocyanate or any other suitable isothiocyanic esters, may be employed in admixture with the ethyl formate.

Typically, the carbon dioxide mixture described above is applied through a spray nozzle and the application rate calculated to meet the commodity or structure being treated. The ethyl formate+isothiocyanic ester formulations can also be added to gaseous carbon dioxide, and allowing the liquid formulation to vaporise and mix with the carbon dioxide prior to or during application. As with all applications protocols, the fumigant formulation may be applied over a period of time, or at intervals to complete the dose or top up previous doses.

Further methods of fumigation include low flow gaseous fumigation, low pressure gaseous fumigation, high pressure gaseous fumigation, spraying of a fumigant in solution and soaking of a commodity in a fumigant and solution. This list is not exhaustive and application of the synergistic formulations of the invention conditions may be altered to best suit the method of fumigation as can be determined by a person skilled in the art. The formulation may be applied as a liquid, gas or vapour dissolved in a carrier gas or through absorbent or absorbent chemical means. As will be understood by persons skilled in the art, fumigation of commodities can be effected by spraying the commodity with a liquid containing the formulation of alternatively, the formulation can be poured onto or into the commodity to cover it or to trickle through it. Probes having small holes may be inserted into grain stores in the application of the fumigants of the invention. Air or any other suitable gas may be bubbled or pushed through the commodity or structure in order to vaporise and/or disperse the fumigant. The contact with the fumigant may be maintained by constant or intermittent application or as a once-off treatment.

The two active components, the alkyl formate and isothiocyanic ester, may be applied as an intimately mixed formulation optionally with a carrier solid, liquid or gas and may be applied simultaneously or sequentially over a short enough interval to achieve the synergistic outcome.

In a highly preferred application, the solid isothiocyanic ester is dissolved in the liquid alkyl formate as a binary active mixture in preparing the formulations of the invention. Without wishing to be limited to theory, it is thought that the partitioning of the isothiocyanic ester in the alkyl formate allows for the vaporisation of the isothiocyanic ester with the alkyl formate. This formulation is thought to provide for a more even distribution of isothiocyanate ester through the structure, space or commodity being fumigated and better absorption gradient across grain than crystalline isothiocyanic esters on their own. This allows for better access to the internal stages of insect or pest biota, particularly *Rhyzopertha dominica* and *Sitophilus oryzae*, in commodities such as grain.

Successful application can also be effected by mixing a gas stream containing alkyl formate with a volatised stream of an isothiocyanic ester. In such cases, it is usual to at least preheat the isothiocyanic ester to effect volatilisation of the solid. The streams may be mixed prior to application to the commodity or structure, or applied separately and mixed therein. It is also possible to pass a gaseous stream of ethyl formate over a heated bed of the solid isothiocyanic ester to effect vaporisation and formation of the synergistic fumigant mixtures of the invention. These and other methods of mixing and/or applying the fumigants to achieve the desired outcome as known to those skilled in the art are within the scope of this invention.

At the end of the fumigation, it is usual that the ethyl formate has naturally decomposed by hydrolysis to ethanol and formic acid. Methyl formate decomposes to methanol and formic acid. Likewise, the isothiocyanic ester residues are found to decline to acceptable levels without aeration. Positive steps may also be taken to remove any remaining fumigant by natural aeration or by flushing the commodity with a clean airstream, although this is not usually required.

It will be understood by persons skilled in the relevant art that the amount of fumigant that is provided to the volume being fumigated varies depending on the level of infestation and the types of species present. The amount of fumigant required is then calculated using a combination of fumigant concentration and exposure time. In general a lower concentration requires an increased duration and a higher concentration is suitable for shorter duration.

Ethyl formate is available as Eranol® supplied by Orica. Likewise, methyl formate is also available. Isothiocyanic esters are available from Sigma Aldrich or as components of mustard oils from brassicas.

The formulations of the invention allow for the successful fumigation of commodities at sublethal concentrations of ethyl formate used on its own. In addition or alternatively, the formulations may be found to be effective over shorter periods of application and/or lower application temperatures than that of an isothiocyanic ester in the absence of an alkyl formate.

The improved formulations are found to be some 2-3 times more effective that ethyl formate alone, and some 4-5 times more effective than methyl isothiocyanate alone.

The fumigant formulations of the invention may also advantageously contain additional fumigants provided that they do not react with or are not deleterious to the alkyl formate or isothiocyanic ester.

If different types of insect or pest biota are being controlled, the concentrations preferably relate to the insect or pest which is most difficult to control. Commodities such as seed, grains, fruit or produce may be fumigated together with their containers such as, for example, transport vehicles (ships, railway trucks, lorries), rooms and buildings (churches, museums, mills), storage rooms (grain stores, silos, bunkers or containers) and smaller buckets (drums, pails and the like). The fumigant composition may advantageously be employed in sealed or enveloped confinements, however it is particularly applicable to grain stores in unsealed silos and bins.

It is preferred that the grain or commodity being treated is at 15° C. or greater when using the ethyl formate formulation as a grain fumigant. Field trials have shown that the ethyl formate formulation of the invention exhibits excellent activity as a fumigant in unsealed farm bins compared to ethyl formate used on its own. Unlike phosphine which takes days to kill insects, the ethyl formate formulation of the invention kills insects and biota rapidly in about 20 hours or less. The formulations are convenient to transport and store and are easy to apply. The synergistic formulations of the invention allow for lower concentrations of ethyl formate to be used coupled with greater pest control and mortality rates across a range of species and life stages. The ethyl formate formulation of the invention makes for a suitable fast kill replacement of methyl bromide which is being phased out in developed countries from 2005.

The inventors of the present invention conducted numerous experiments to demonstrate the improved effect of isothiocyanic esters with alkyl formates as fumigant formulations. A number of these non-limiting experiments are detailed in the examples which follow.

EXAMPLES

1. Stability Studies

The stability of ethyl formate and methyl isothiocyanate as a fumigant formulation stored at 25° C. was assessed for a period of 1 day, 1 month and 2 months. Table 1 below shows the percent of the original fumigant present (M/Mo) after different periods of storage. This is also graphically represented in FIG. 1. The results show that both ethyl formate and methyl isothiocyanate when formulated are stable during storage for 2 months.

TABLE 1

Ethyl formate and methyl isothiocyanate formulation stability (M/Mo)

|  | 1 Day | 1 Month | 2 Months |
|---|---|---|---|
| EtF | 100 | 102 | 98.5 |
| MITC | 100 | 98 | 101.5 |

2. Toxicity Studies

Figure 2:
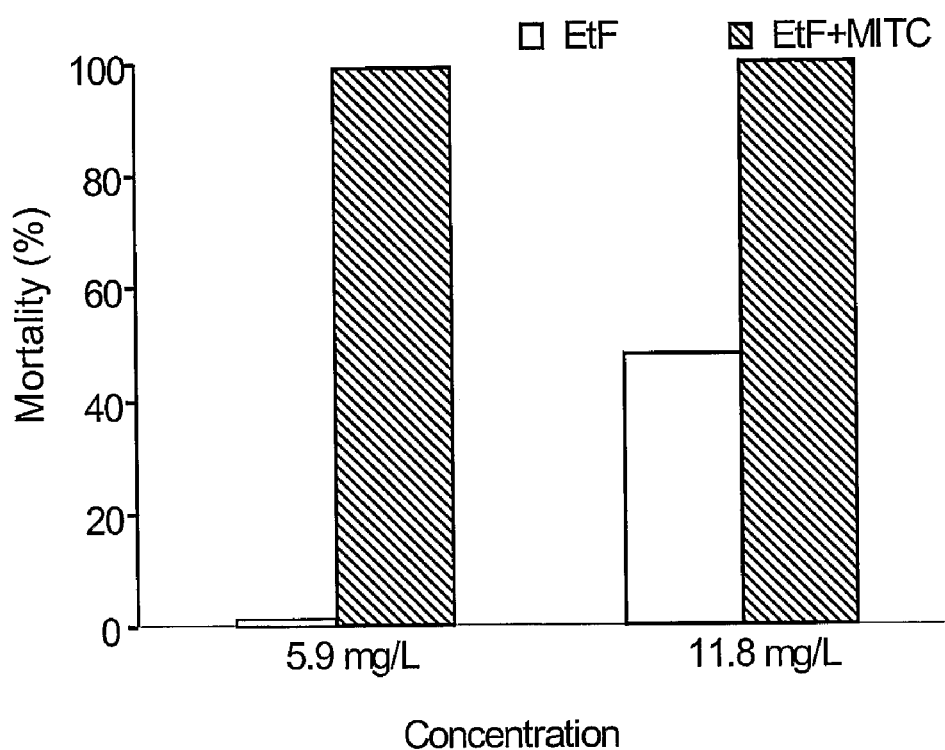
FIG. 2 graphically represents a comparison of the toxicity of ethyl formate alone and ethyl formate+methyl isothiocyanate to adults of Sitophilus oryzae at 25° C. and 24 hours fumigation for two concentrations of fumigant.

Toxicity studies of ethyl formate alone compared with ethyl formate and ethyl isothiocyanate were conducted on adults of the rice weevil *Sitophilus oryzae* at 25° C. and 24 hours fumigation. The toxicity studies were conducted at concentrations of 5.9 mg/L and 11.8 mg/L. The results are shown in table 2 below and FIG. 2.

TABLE 2

Mortality studies of adult *S. oryzae* with ethyl formate alone and ethyl formate and methyl isothiocyanate (mortality %)

|  | 5.9 mg/L | 11.8 mg/L |
|---|---|---|
| EtF | 0 | 48 |
| EtF + MITC | 99 | 100 |

The toxicity studies show that adults of *S. oryzae* were unaffected by fumigation for 24 hours at 25° C. at a concentration of 5.9 mg/L of ethyl formate. Up addition of 5% methyl isothiocyanate, there was observed a 99% mortality of the *S. oryzae* adults showing quite remarkable synergism between the ethyl formate and methyl isothiocyanate. Doubling the fumigant concentration to 11.8 mg/L showed 48% mortality with ethyl formate alone compared to 100% mortality of *S. oryzae* adults with the ethyl formate/methyl isothiocyanate formulation of the invention.

Figure 3:
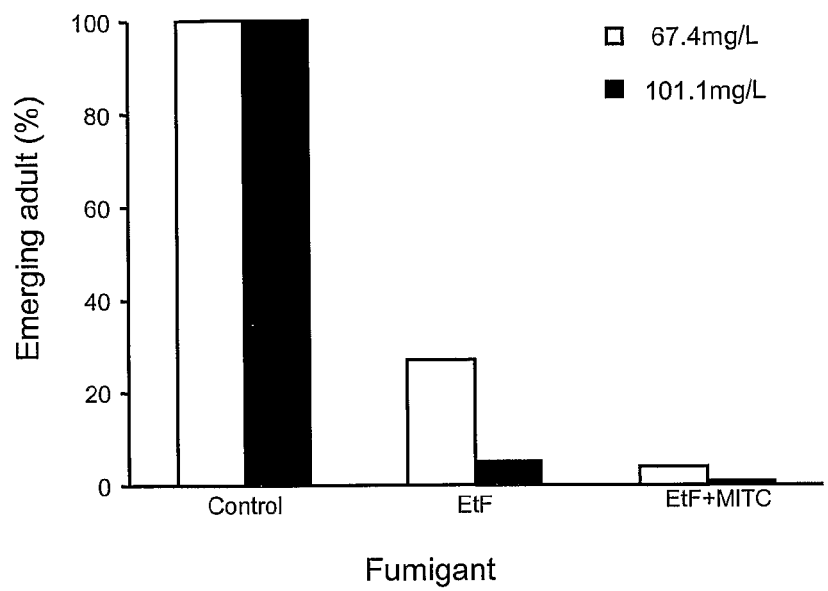
FIG. 3 graphically represents a comparison of the toxicity of ethyl formate alone and ethyl formate+methyl isothiocyanate to mixed aged cultures (egg, larvae and pupae) of Sitophilus oryzae at 25° C. and 6 hours fumigation for two concentrations of fumigant.

Table 3 compares the toxicity of ethyl formate alone and ethyl formate+methyl isothiocyanate to mixed aged cultures (egg, larvae and pupae) of *S. oryzae* at 25° C. after 6 hours fumigation at two concentrations. These results are graphically represented in FIG. 3.

TABLE 3

Emerging adult studies to mixed aged cultures of *S. oryzae* with ethyl formate alone and ethyl formate + methyl thiocyanate.

|  | Control | EtF | EtF + MITC |
|---|---|---|---|
| 67.4 mg/L | 100 | 27 | 3 |
| 101.1 mg/L | 100 | 5 | 0 |

The results show that ethyl formate alone at a concentration of 67.4 mg/L acts as a fumigant against mixed aged cultures of *S. oryzae* limiting the emerging adult population to 27% of that of a control sample. In comparison, the ethyl formate+ethyl thiocyanate fumigant composition of the invention of the same concentration dramatically reduces the emerging adult population to 3% of the control. At a higher concentration of 101.1 mg/L, ethyl formate alone further reduces the emerging adult population to 5% of that of the control. In comparison, the ethyl formate+methyl isothiocyanate formulation at the height concentration completely stops the mixed aged cultures from reaching adult stage.

Figure 4:
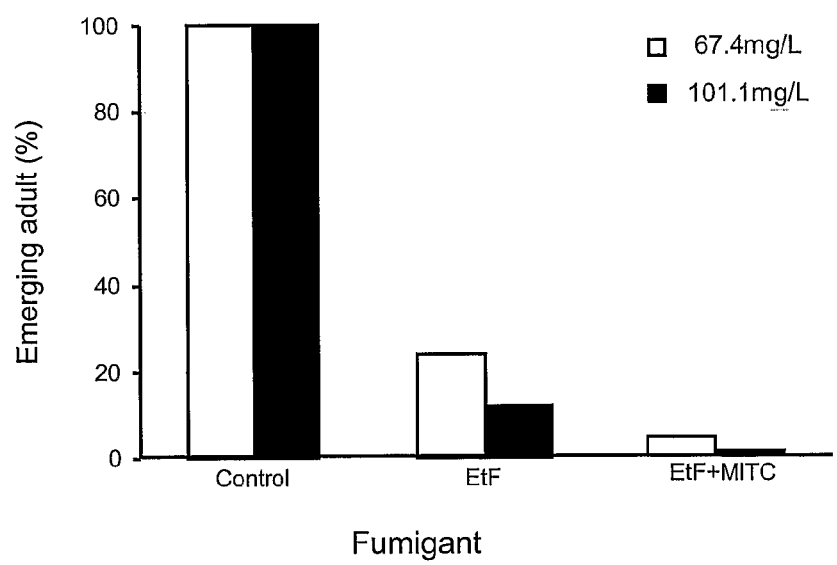
FIG. 4 graphically represents a comparison of the toxicity of ethyl formate alone and ethyl formate+methyl isothiocyanate to pupae of Sitophilus oryzae at 25° C. at 6 hours fumigation for two concentrations of fumigant.

Table 4 compares the toxicity of ethyl formate alone and ethyl formate+methyl isothiocyanate to pupae of *S. oryzae* at 25° C. after 6 hours fumigation at two concentrations. These results are graphically represented in FIG. 4.

TABLE 4

Emerging adult studies to the pupae of *S. oryzae* with ethyl formate alone and ethyl formate + methyl isothiocyanate for 6 hours fumigation (emerging adult %)

|  | Control | EtF | EtF + MITC |
|---|---|---|---|
| 67.4 mg/L | 100 | 24 | 1 |
| 101.1 mg/L | 100 | 12 | 0 |

The results show that ethyl formate alone at a concentration of 67.4 mg/L acts as a fumigant against pupae of *S. oryzae* limiting the emerging adult population to 24% of that of a control sample. In comparison, the ethyl formate+methyl isothiocyanate fumigant composition of the invention of the same concentration dramatically reduces the emerging adult population to only 1% of the control. At a higher concentration of 101.1 mg/L, ethyl formate alone further reduces the emerging adult population to 12% of that of the control. In comparison, the ethyl formate+methyl isothiocyanate formulation at the higher concentration completely stops the pupae from reaching adult stage.

Figure 5:
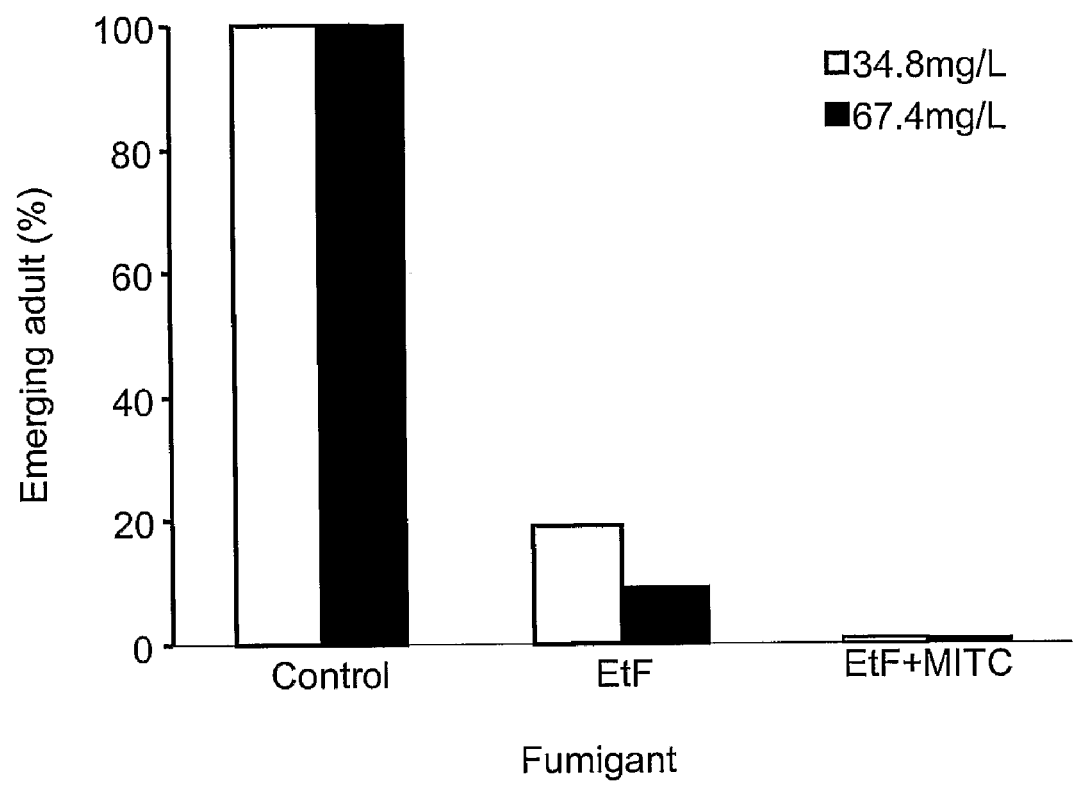
FIG. 5 graphically represents a comparison of the toxicity of ethyl formate alone and ethyl formate+methyl isothiocyanate to the pupae stage of Sitophilus oryzae at 25° C. and 24 hours fumigation for two concentrations of fumigant.

Table 5 compares the toxicity of ethyl formate alone and ethyl formate+methyl isothiocyanate to pupae of *S. oryzae* at 25° C. after 24 hours fumigation at two concentrations. These results are graphically represented in FIG. 5.

TABLE 5

Emerging adult studies to the pupae of *S. oryzae* with ethyl formate alone and ethyl formate + methyl isothiocyanate for 24 hours fumigation (emerging adult %)

|  | Control | EtF | EtF + MITC |
|---|---|---|---|
| 34.8 mg/L | 100 | 19 | 0 |
| 67.4 mg/L | 100 | 9 | 0 |

The results show that ethyl formate alone at a concentration of 34.8 mg/L acts as a fumigant against pupae of *S. oryzae* limiting the emerging adult population to 19% of that of a control sample, and limiting to 9% at a concentration of 67.4 mg/L. In comparison, the ethyl formate+methyl isothiocyanate formulations at both concentrations completely stop the pupae from reaching adult stage.

3. 54 kg Wheat Cylinder Trial

Figure 6:
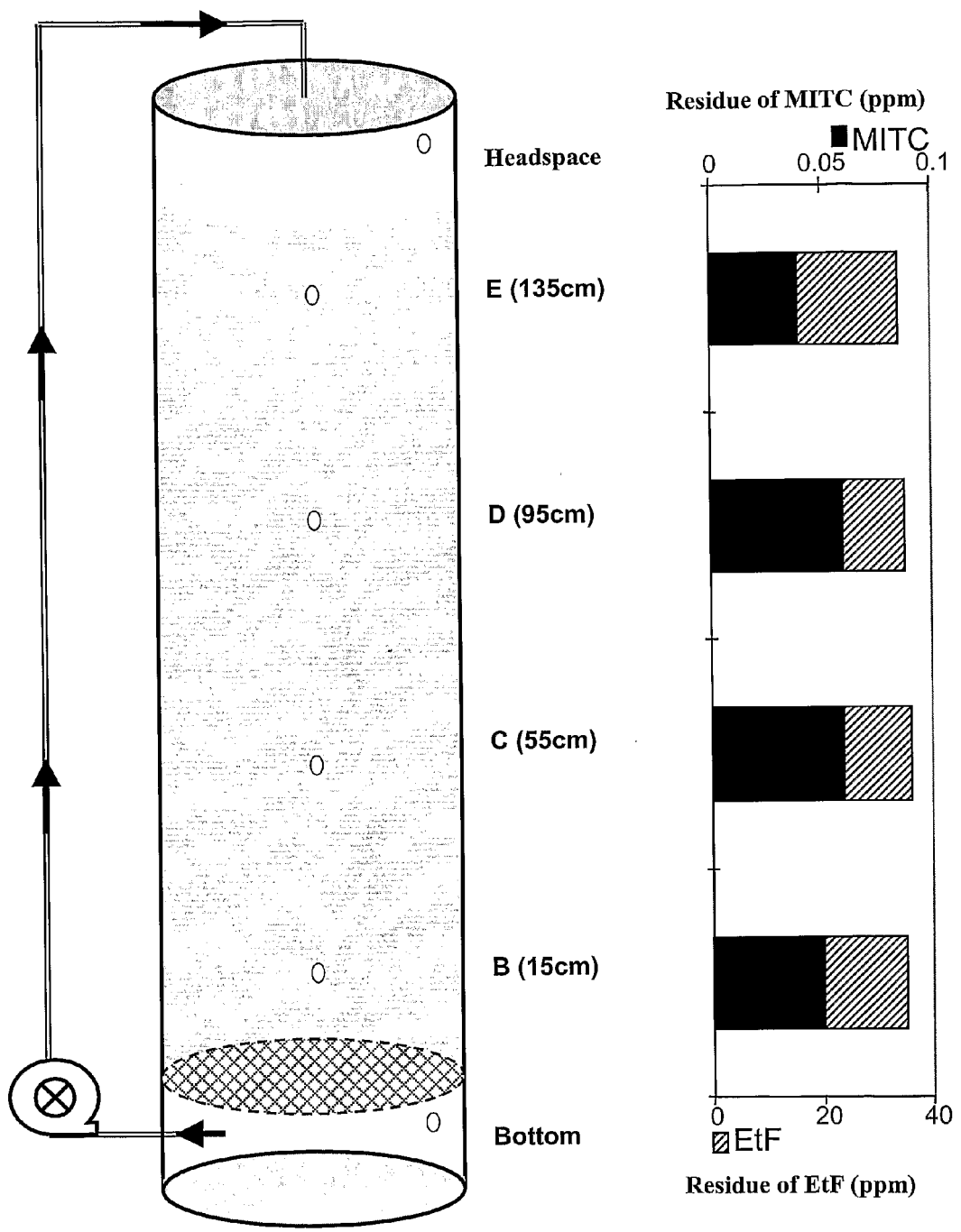
FIG. 6 schematically represents a 75.8 L (Ø=24.2 cm and h=165 cm) polyvinyl chloride cylinder containing 52 kg of wheat. Ethyl formate and methyl isothiocyanate residue concentrations are shown from wheat samples taken at different locations in the cylinder after 7 days fumigation without aeration.

A cylinder of wheat was fumigated with a 95:5 (w:w) ratio of ethyl formate+methyl isothiocyanate for seven days without aeration. The cylinder was made of polyvinyl chloride having a volume of 75.8 L (Ø=24.2 cm and h=165 cm) and contained 52 kg of wheat and is shown in FIG. 6. The wheat was dosed with the ethyl formate/methyl isothiocyanate formulation at a rate of 80 g/t and subjected to a low rate of recirculated air (1 gas exchange/hour).

A comparison of the ethyl formate and methyl isothiocyanate residues in fumigated wheat at different locations of the cylinders is also shown in FIG. 6. The wheat was fumigated for 7 days without aeration. The ethyl formate and methyl isothiocyanate fumigants were found to penetrate throughout the cylinder of wheat and even distribution of the fumigants was achieved. After the 7 days fumigation without aeration, the ethyl formate residues were reduced to 37 ppm whilst the ethyl isothiocyanate residues were reduced to 0.06 ppm and lower.

Figure 7:
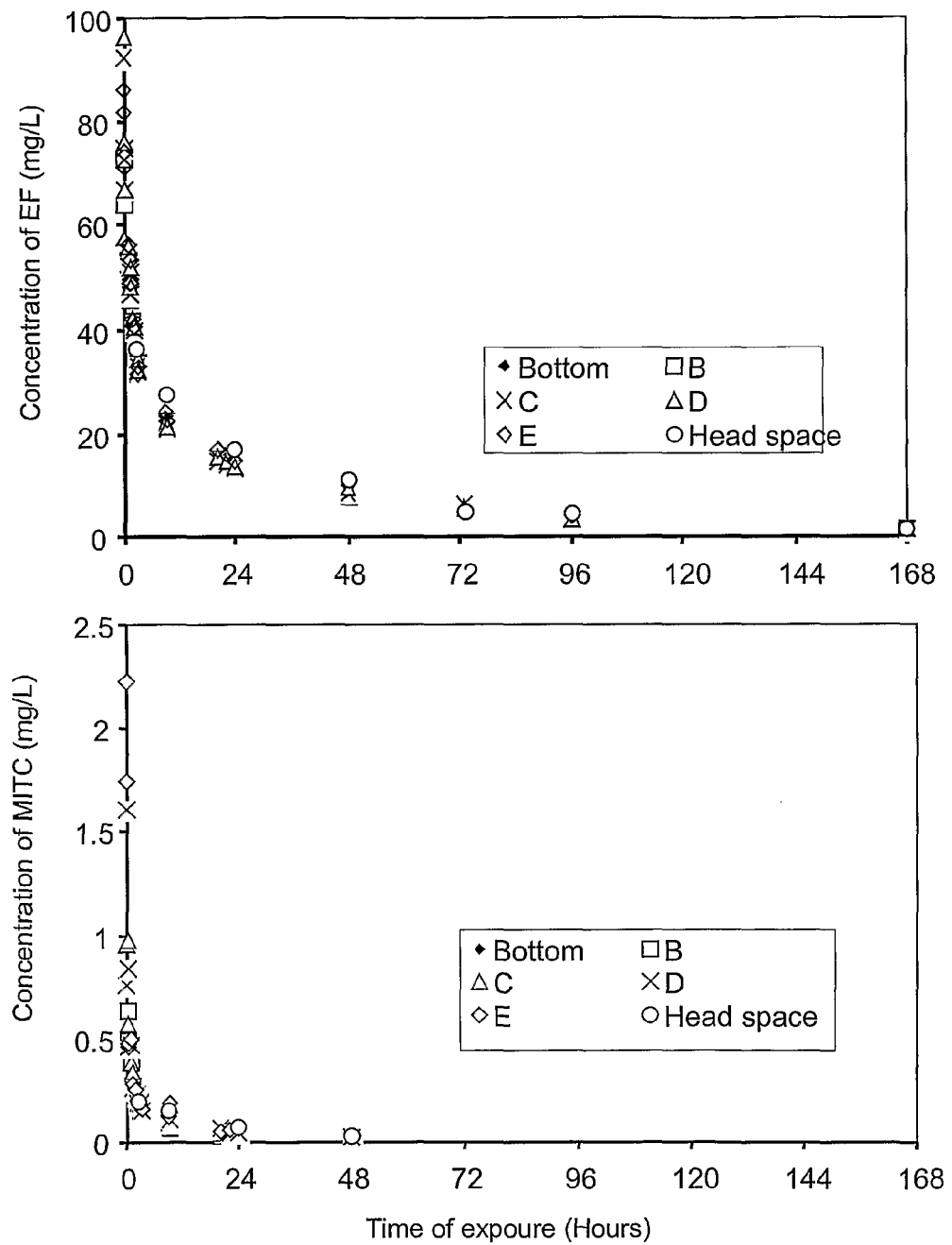
FIG. 7 graphically represents the concentration of ethyl formate and methyl isothiocyanate in a cylinder of wheat (95% filling ratio) over 7 days of fumigation at room temperature.

The concentrations of ethyl formate and methyl isothiocyanate were found to decay rapidly at an exponential rate during the 7 days of fumigation in the cylinder of wheat (95% filling ratio) at room temperature. FIG. 7 plots the drop in concentration of each of the fumigant components over time during the 7 day fumigation experiment.

These studies were extended to the insect species *Tribolium castaneum* and *Rhyzopertha dominica*. Bioassay studies showed that all stages of the insect species tested were completely killed.

4. 1 Tonne Bin Trials

Figure 8:
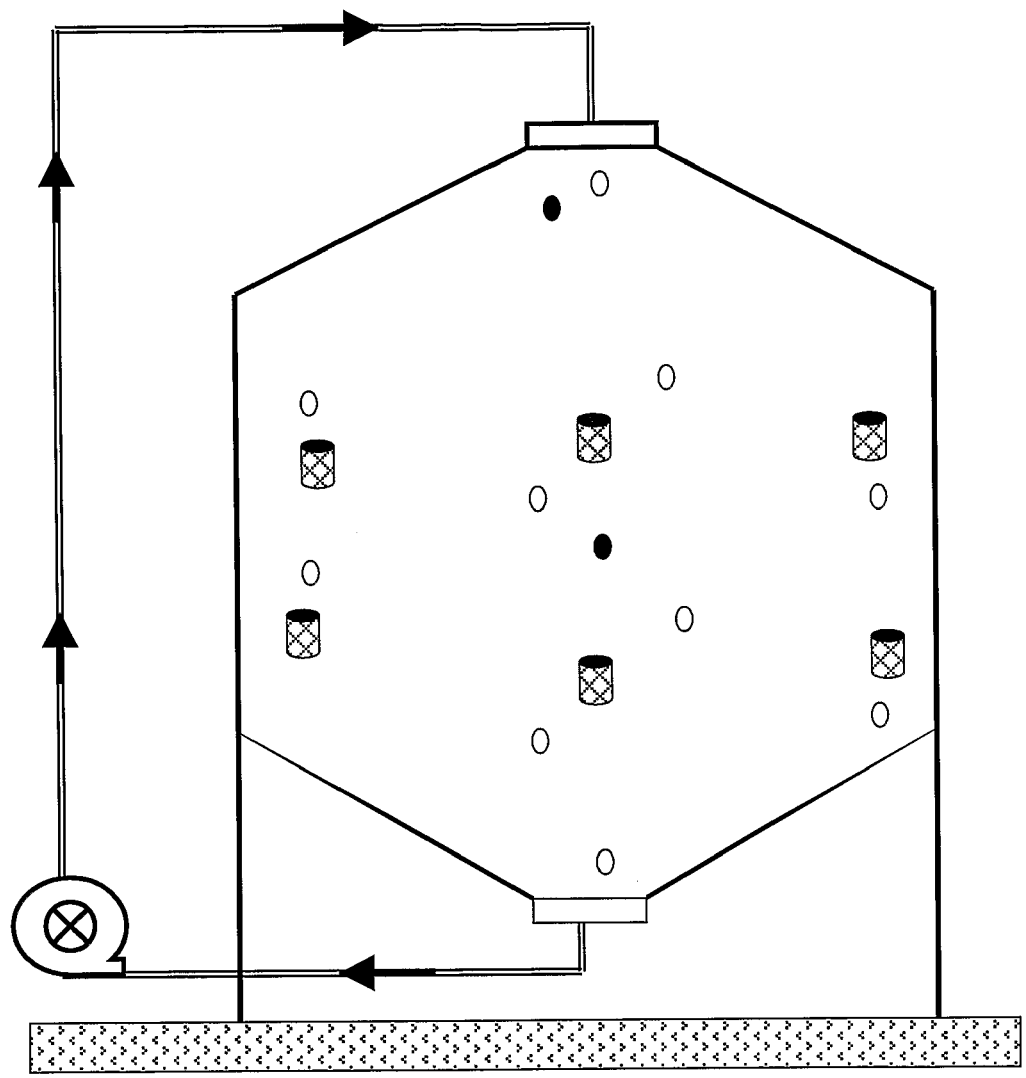
FIG. 8 schematically represents a 1.35 $m^3$ (Ø=100 cm and h=172 cm) metal bin containing 1 tonne of wheat.

A bin of wheat was fumigated with a 95:5 (w:w) ratio of ethyl formate+methyl isothiocyanate for seven days without aeration. The metal bin had a volume of 1.35 m³ and contained 1 tonne of wheat. The bin is shown in FIG. 8. The wheat was dosed with the ethyl formate+methyl isothiocyanate formulation at a rate of 80 g/t and subjected to a low rate of recirculated air (1 gas exchange/hour) and fumigated for 7 days.

Figure 9:
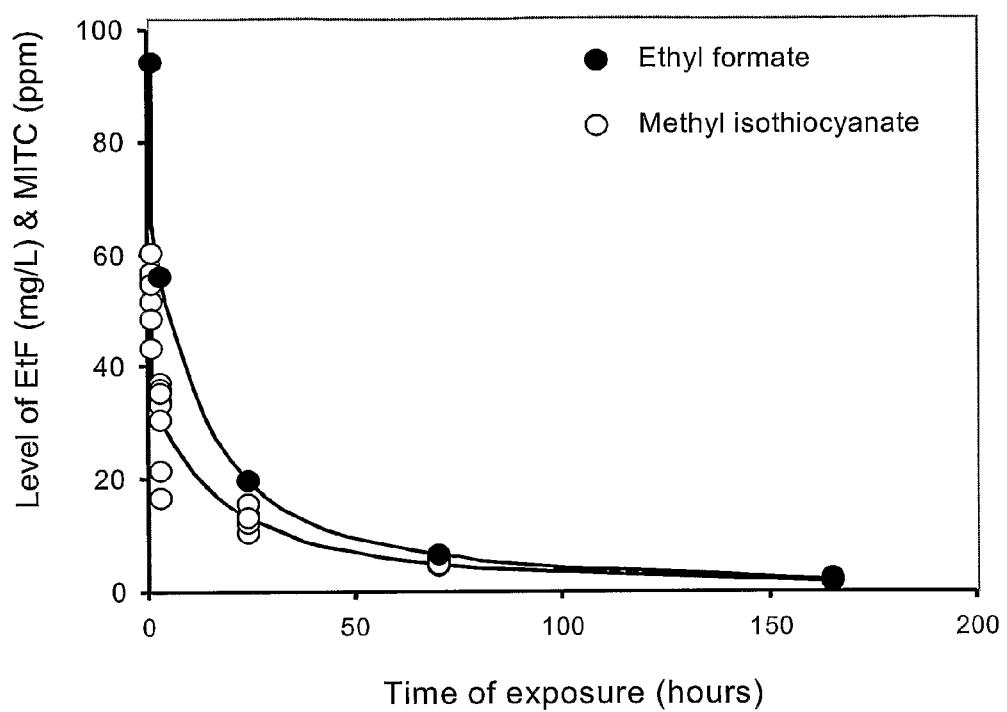
FIG. 9 graphically represents the concentration of ethyl formate and methyl isothiocyanate in a 1 tonne bin of wheat (95% filling ratio) over 7 days of fumigation at room temperature (● is concentration of ethyl formate and ○ is concentration of MITC).

The concentrations of ethyl formate and methyl isothiocyanate were found to decay rapidly at an exponential rate during the 7 days of fumigation in the cylinder of wheat (95% filling ratio) at room temperature. FIG. 9 plots the drop in concentration of each of the fumigant components over time during the 7 day fumigation experiment.

These studies were extended to the insect species *Tribolium castaneum* and *Rhyzopertha dominica*. Bioassay studies showed that all stages of the insect species tested were completely killed.

5. 4 Tonne Outloading Trials

Figure 10:
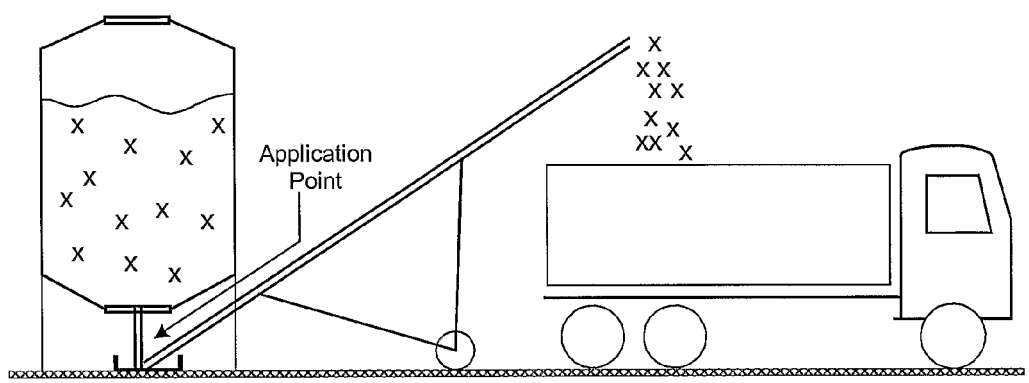
FIG. 10 schematically represents the application of an ethyl formate+methyl isothiocyanate composition to grain from a bin during outloading of the grain via an auger into a truck.

During outloading, wheat was treated/fumigated with a 95:5 (w:w) ratio of ethyl formate+methyl isothiocyanate at a rate of 160 g/t. The treated wheat was then transferred by auger into a 4 tonne truck tray and then covered and held overnight (see FIG. 10).

The concentrations of ethyl formate and methyl isothiocyanate were found to decay rapidly at an exponential rate during overnight of fumigation in the tray of wheat (100% filling ratio) at 20° C. temperature. On the next day, the concentration of each of the fumigant components was found to have dropped down below TLV, and all *Tribolium castaneum*, *Rhyzopertha dominica* and *Sitophilus oryzae* adults were killed.

6. 55 Tonne Silo Field Trials

A silo of wheat was fumigated with a 95:5 (w:w) ratio of either ethyl formate+methyl isothiocyanate or ethyl formate+allyl isothiocyanate without aeration. The capacity of the silo was 55 tonne and contained 50 tonne of grain. The wheat was dosed with the EtF+MITC or EtF+AITC at a rate of 80 g/t and subjected to a low rate of recirculated air (1 gas exchange/hour) and fumigated for 7 days.

It was found that the two fumigant formulations were effective in killing all insect species tested with no effect on germination and seed colour of treated wheat. After 7 days exposure the residues were down to background levels of ethyl formate and methyl or allyl isothiocyanate without aeration. The results are shown in Table 6 below.

TABLE 6

Mortality studies of pest biota with ethyl formate + methyl isothiocyanate or ethyl formate + allyl isothiocyanate on silo quantities of wheat

| | | | |
|---|---|---|---|
| Location | Canberra | Canberra | Brisbane |
| Commodity | Wheat | Wheat | Wheat |
| Capacity of silo | 55 t | 55 t | 50 t |
| Quantity of grain | 50 t | 50 t | 50 t |
| Grain Temperature | 20-23° C. | 20-23° C. | 22-24° C. |
| Formulations | EtF + MITC (95:5, v/w) | EtF + AITC (95:5, v/w) | EtF + MITC (95:5, v/w) |
| Dosage | 80 g/t of grain | 80 g/t of grain | 80 g/t of grain |
| Application | Pour from top of silo | Pour from top of silo | Pour from top of silo |
| Recirculation | 1 air exchange/hr | 1 air exchange/hr | 1 air exchange/hr |
| Bioassay results | 100% kill insects at all stages: *T. castaneum* *T. variabile* *R. dominica* *S. oryzae* *O. surinamensis* | 100% kill insects at all stages: *T. castaneum* *T. variabile* *R. dominica* *S. oryzae* *O. surinamensis* | 100% kill insects at all stages: *T. castaneum* *R. dominica* *S. oryzae* |
| Quality of wheat | No effect on generation and seed colour of treated wheat | No effect on generation and seed colour of treated wheat | No effect on generation and seed colour of treated wheat |
| Residues | 7 days exposure reduce to background levels of EtF and MITC without aeration | 7 days exposure reduce to background levels of EtF and AITC without aeration | 7 days exposure reduce to background levels of EtF and MITC without aeration |

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification individually or collectively, and any and all combinations of any two or more of said steps or features.

The reference to any prior art in this specification is not, and should not be taken as, an acknowledgment or any form of suggestion that that prior art forms part of the common general knowledge in the field of endeavour.

The invention claimed is:

1. A synergistic fumigant composition consisting of about 60 to about 99.5 parts w/w of ethyl formate and about 40 to 0.5 parts w/w of methyl isothiocyanate.

2. A method of delivering a fumigant composition to a commodity, structure or space, wherein the method comprises the steps of applying a synergistic fumigant composition consisting of about 60 to about 99.5 parts w/w of ethyl formate and about 40 to 0.5 parts w/w of methyl isothiocyanate to said commodity, structure or space, and vapourising the fumigant mixture.

3. The method of claim 2, wherein the commodity is stored grain or the structure or space holds or contains stored grain.

4. The method of claim 2, wherein the commodity is stored grain and the fumigant mixture kills the internal stages of pest biota within the stored grain.

5. A method of fumigation, comprising the step of applying an effective amount of a synergistic fumigant composition consisting of about 60 to about 99.5 parts w/w of ethyl formate and about 40 to 0.5 parts w/w of methyl isothiocyanate in the gaseous form or in solution, in association with a carrier gas, to a commodity and/or structure and/or space.

6. The method of claim 5 wherein the carrier gas is an inert gas having a low oxygen concentration.

7. The method of claim 5 wherein the carrier gas is an inert gas having a low oxygen concentration and contains carbon dioxide.

8. A method of claim 2, wherein the commodity is selected from grain, seed, meat, fruit, dried fruit, vegetables, timber, plants, cut flowers and soil.

9. A method of claim 2, wherein the structure and/or space is a farm bin, silo, container, room or premises, flour mill or rice mill or food processing factory, supermarket, museum.

* * * * *